US005591879A

United States Patent [19]
Frey et al.

[11] Patent Number: 5,591,879
[45] Date of Patent: Jan. 7, 1997

[54] PROCESS FOR PREPARING CYCLOPENTADIENYL-TYPE LIGANDS

[75] Inventors: Krisztina Frey; Gabriele von Massow; Helmut G. Alt, all of Bayreuth, Germany; M. Bruce Welch, Bartlesville, Okla.

[73] Assignee: Phillips Petroleum Company, Bartlesville, Okla.

[21] Appl. No.: 444,985

[22] Filed: Jun. 23, 1995

Related U.S. Application Data

[62] Division of Ser. No. 303,982, Sep. 9, 1994.

[51] Int. Cl.$^6$ .................. C07F 7/08; C07F 7/10
[52] U.S. Cl. .............. 556/404; 556/410; 556/413
[58] Field of Search .................. 556/404, 410, 556/413

[56] References Cited

U.S. PATENT DOCUMENTS

| | | | |
|---|---|---|---|
| 4,173,590 | 11/1979 | Schmidbauer | 260/606.5 P |
| 4,837,226 | 6/1989 | Coughenour et al. | 514/443 |
| 5,096,867 | 3/1992 | Canich | 502/103 |
| 5,155,080 | 10/1992 | Elder et al. | 505/152 |
| 5,191,132 | 3/1993 | Patsidis et al. | 585/375 |
| 5,208,357 | 5/1993 | Mintz | 556/43 |
| 5,227,440 | 7/1993 | Canich et al. | 526/129 |
| 5,272,236 | 12/1993 | Lai et al. | 526/348.5 |
| 5,349,100 | 9/1994 | Mintz | 556/53 |
| 5,371,256 | 12/1994 | Togni et al. | 556/14 |
| 5,474,716 | 12/1995 | Lisowsky | 556/413 X |

OTHER PUBLICATIONS

"Reactions of [Diphenylphosphino)methyl]lithium with Dimethylfulvene", Schore and Labelle, J. Org. Chem. 1981, 46, pp. 2306–2310.

"Indirect Metal–Metal Linkage: Cyclic Ferrocene Complexes with a Second Metal Linked via Remote Phosphine Functionality", Schore et al., Inorg. Chem. 1981, vol. 20, 3200–08.

"Synthesis of [C$_5$(CH$_3$)4H]CH$_2$CH$_2$CH$_2$P(C$_6$H$_5$)$_2$: A Novel Heterodifunctional Ligand Possessing Both a Tetramethylcyclopentadiene and a Remote Diphenylphosphine Functionality", Bensley et al., J. Org. Chem. 1988, 53, pp. 4417–4419.

"New Heterodifunctional Ligands for Organotransition–Metal Chemistry: Ph$_2$P(CH$_2$)$_n$(c$_5$Me$_4$H(n=0,2)", Szymoniak et al., J. Org. Chem., 1990, 55, pp. 1429–1432.

"Synthesis of (C$_6$H$_5$)$_2$PCH$_2$Si(CH$_3$)$_2$C$_5$H$_4$Li: A novel heterodiifunctional System for the Directed Linkage of Dissimilar Transition Metal Fragments", Schore, J. Am. Chem. Soc., 101, 7410–12, Nov. 21, 1979.

"Complexes Du Titane Et Du Zirconium Contenant Les Ligands Cyclopentadienylphenylphosphine et cyclopentadienylethyldiphenylphosphine: Access a des Structures Heterobimetallizues", LeBlank et al., J. Organomet. Chem. 231, 1986.

"Cyclic Conjugate 5– and 7–ring systems. I. Synthesis and reactions of fulvenecarboxaldehydes", Kitsuta, Chem. Abstracts vol. 59, 2706–07, 1963.

"An Exceptionally Simple and Efficient Method for the Preparation of a Wide Variety of Fulvenes", Stone et al., J. Org. Chem. vol. 49, No. 11, Jun. 1984.

Journal of Organometallic Chemistry, 456 (1993) 89–85, "Zirkonocenkomplexe mit einem funktionalisierten Cyclopentadienylliganden. Molekulstruktur von ($\eta^5$:$\eta^2$–C$_5$H$_4$CMe$_2$C$_9$H$_7$)Zr)(PMe$_3$)", Helmut G. Alt et al.

*Primary Examiner*—Paul F. Shaver
*Attorney, Agent, or Firm*—Carl D. Corvin

[57] ABSTRACT

In accordance with the present invention there is provided a cyclopentadienyl-type ligand represented by the formula ZA, wherein Z is a cyclopentadienyl-type group, wherein A is —YPR$_2$, —YNR$_2$, or —NR$_2$, wherein Y is an alkylene group containing 1 to 24 carbon atoms, wherein each R is individually selected from alkyl groups containing 1 to 20 carbon atoms. Another aspect of the invention is to provide a metallocene represented by the formula ZAMX$_3$, wherein Z and A are as described above, M is a Group IVB or VB transition metal, and X is a halide. Other aspects of the present invention include catalyst systems comprising the metallocenes and an organoaluminoxane, processes for preparing the above defined ligands, metallocenes and catalyst systems, and polymerization processes employing the catalyst systems.

9 Claims, No Drawings

PROCESS FOR PREPARING CYCLOPENTADIENYL-TYPE LIGANDS

This is a divisional of copending application Ser. No. 08/303,982, filed Sep. 9, 1994.

The present invention relates to the preparation of heterodifunctional cyclopentadienyl-type ligands and metallocenes.

BACKGROUND OF THE INVENTION

Cyclopentadienyl-type ligands have found a number of uses in the past. As used herein, the term cyclopentadienyl-type ligands includes ligands containing a cyclopentadienyl-type group. Cyclopentadienyl-type groups as used herein contain a cyclopentadienyl functionality and include unsubstituted cyclopentadienyl, substituted cyclopentadienyl, unsubstituted indenyl, substituted indenyl, unsubstituted fluorenyl, and substituted fluorenyl groups. Such ligands have utility in the preparation of metallocenes useful for the polymerization of olefins.

Other applications for metallocenes include asymmetric hydrogenation, alkene epoxidation, alkene isomerization, ketone reduction, and as stoichiometric reagents for stereoselective cobalt-mediated reactions, allyltitanium addition reactions with aldehydes, and the highly selective formation of allylic amines.

It would therefore be desirable to produce a variety of novel ligands from readily available materials employing a simple and economical process.

SUMMARY OF THE INVENTION

An object of the present invention is to provide an economical and simple processes for preparing new cyclopentadienyl-type ligands.

Another object of the present invention is to provide a variety of cyclopentadienyl-type ligands useful in preparing metallocenes.

Another object of the present invention is to provide various metallocenes useful in the polymerization of olefins.

Another object of the present invention is to provide processes for preparing new metallocenes.

Another object of the present invention is to provide catalyst systems capable of polymerizing olefins.

Another object of the present invention is to provide processes for preparing catalyst systems.

Another object of the present invention is to provide olefin polymerization processes employing the catalyst systems.

In accordance with the present invention there is provided cyclopentadienyl-type ligands represented by the formula ZA, wherein Z is a cyclopentadienyl-type group and wherein A is $-YPR_2$, $-YNR_2$, or $-NR_2$ wherein Y is an alkenyl or substituted alkenyl group containing 1 to 24 carbon atoms and wherein each R is individually selected from alkyl groups containing 1 to 20 carbon atoms. Another aspect of the invention is to provide metallocenes represented by the formula $ZAMX_3$, wherein Z and A are as described above, M is a Group IVB or VB transition metal, and X is a halide. Other aspects of the present invention include catalyst systems comprising the metallocenes and an organoaluminoxane, processes for preparing the above defined ligands, metallocenes and catalyst systems, and polymerization processes employing the catalyst systems.

DETAILED DESCRIPTION OF THE INVENTION

The cyclopentadienyl-type ligands of the present invention are represented by the formula ZA, wherein Z is a cyclopentadienyl-type group and A is $-YPR_2$, $-YNR_2$, or $-NR_2$, wherein Y is an alkylene group containing 1 to 24 carbon atoms, wherein each R is individually selected from alkyl groups containing 1 to 20 carbon atoms, preferably 1 to 10 carbon atoms, more preferably 1 to 5 carbon atoms, and most preferably the R groups are methyl or ethyl. Preferably Y contains 1 to 20 carbon atoms, more preferably 1 to 16 carbon atoms, and most preferably Y is an unsubstituted or substituted methylene or ethylene group. Some examples of Y include methylene, ethylene, dimethylmethylene, dimethylethylene, phenylethylene, butylethylene, diphenylethylene, propylene, and butylene. Some examples of R include methyl, ethyl, propyl, isopropyl, butyl, tert-butyl, isobutyl, amyl, isoamyl, hexyl, cyclohexyl, heptyl, octyl, nonyl, decyl, cetyl, 2-ethylhexyl. Excellent results have been obtained when R is methyl and those compounds are preferred. In the following examples Me is methyl, Et is ethyl, Ph is phenyl, and t-Bu is tert-butyl. Typical examples of A include $-CH_2PMe_2$, $-CH_2CH_2PMe_2$, $-CMe_2PMe_2$, $-CMe_2CH_2PMe_2$, $-CPhHCH_2PMe_2$, $-CPh_2CH_2PMe_2$, $-C(t-Bu)HCH_2PMe_2$, $-CH_2PMe_2$, $-CH_2CH_2PMe_2$, $-CMe_2PMe_2$, $-CMe_2CH_2PMe_2$, $-CPhHCH_2PMe_2$, $-CPh_2CH_2PMe_2$, $-C(t-Bu)HCH_2PMe_2$, $-CHPEt_2$, $-CH_2CH_2PEt_2$, $-CMe_2PEt_2$, $-CMe_2CH_2PEt_2$, $-CPhHCH_2PEt_2$, $-CPh_2CH_2PEt_2$, $-C(t-Bu)HCH_2PEt_2$, $-CH_2PEt_2$, $-CH_2CH_2PEt_2$, $-CMe_2PEt_2$, $-CMe_2CH_2PEt_2$, $-CPhHCH_2PEt_2$, $-CPh_2CH_2PEt_2$, $-C(t-Bu)HCH_2PEt_2$, $-CH_2NMe_2$, $-CH_2CH_2NMe_2$, $-CMe_2NMe_2$, $-CMe_2CH_2NMe_2$, $-CPhHCH_2NMe_2$, $-CPh_2CH_2NMe_2$, $-C(t-Bu)HCH_2NMe_2$, $-CH_2NMe_2$, $-CH_2CH_2NMe_2$, $-CMe_2NMe_2$, $-CMe_2CH_2NMe_2$, $-CPhHCH_2NMe_2$, $-CPh_2CH_2NMe_2$, $-C(t-Bu)HCH_2NMe_2$, $-CH_2NEt_2$, $-CH_2CH_2NEt_2$, $-CMe_2NEt_2$, $-CMe_2CH_2NEt_2$, $-CPhHCH_2NEt_2$, $-CPh_2CH_2NEt_2$, $-C(t-Bu)HCH_2NEt_2$, $-CH_2NEt_2$, $-CH_2CH_2NEt_2$, $-CMe_2NEt_2$, $-CMe_2CH_2NEt_2$, $-CPhHCH_2NEt_2$, $-CPh_2CH_2NEt_2$, $-C(t-Bu)HCH_2NEt_2$, $-NMe_2$, and $-NEt_2$.

As noted above, cyclopentadienyl-type group as used herein is a group containing a cyclopentadienyl functionality and is an unsubstituted cyclopentadienyl, substituted cyclopentadienyl, unsubstituted indenyl, substituted indenyl, unsubstituted fluorenyl, or substituted fluorenyl group. The substituents on the cyclopentadienyl-type group can include hydrocarbyl groups containing 1 to 12 carbon atoms, alkoxy groups containing 1 to 12 carbon atoms, trialkylsilyl groups where each alkyl contains 1 to 12 carbon atoms, alkyl halide groups where the alkyl contains 1 to 12 carbon atoms, or halide. Preferably the substituents containing alkyl groups contain 1 to 10 carbon atoms, more preferably 1 to 6 carbon atoms. Some examples of substituents include methyl, ethyl, propyl, butyl, tert-butyl, isobutyl, amyl, isoamyl, hexyl, cyclohexyl, heptyl, octyl, nonyl, decyl, dodecyl, 2-ethylhexyl, pentenyl, butenyl, phenyl, chloride, bromide, and iodide.

Examples of typical cyclopentadienyl-type ligands include

[1-phenyl-2-(dimethylphosphino)ethyl]cyclopentadiene,

[1,1-dimethyl-2-(dimethylphosphino)ethyl]cyclopentadiene,

[1,1-diphenyl-2-(dimethylphosphino)ethyl]cyclopentadiene,

[1-methyl-1-phenyl-2-(dimethylphosphino)ethyl]cyclopentadiene,
[1-tert-butyl-2-(dimethylphosphino)ethyl]cyclopentadiene,
[1-phenyl-2-(dimethylphosphino)ethyl]indene,
[1,1-dimethyl-2-(dimethylphosphino)ethyl]indene,
[1,1-diphenyl-2-(dimethylphosphino)ethyl]indene,
[1-methyl-1-phenyl-2-(dimethylphosphino)ethyl]indene,
[1-tert-butyl-2-(dimethylphosphino)ethyl]indene,
9-(trimethylsilyl)-9-(1-(2-dimethylphosphino)ethyl)fluorene,
9-(1-(2-dimethylphosphino)ethyl)fluorene,
[(dimethylamino)methyl)]cyclopentadiene,
[(diethylamino)methyl) ]cyclopentadiene,
[(dimethylamino)(methyl)(phenyl)methyl)]cyclopentadiene,
[(diethylamino)(methyl)(phenyl)methyl)]cyclopentadiene,
[(dimethylamino)(phenyl)methyl)]cyclopentadiene,
[(diethylamino)(phenyl)methyl)]cyclopentadiene,
[1-phenyl-2-(diethylamino)ethyl]cyclopentadiene,
[1-phenyl-2-(dimethylamino)ethyl)]cyclopentadiene,
[1-phenyl-2-(dimethylamino)ethyl]cyclopentadiene,
[1,1-dimethyl-2-(dimethylamino)ethyl]cyclopentadiene,
[1,1-diphenyl-2-(dimethylamino)ethyl]cyclopentadiene,
[1-methyl-1-phenyl-2-(dimethylamino)ethyl]cyclopentadiene,
[1-tert-butyl-2-(dimethylamino)ethyl]cyclopentadiene,
[1-phenyl-2-(dimethylamino)ethyl]indene,
[1,1-dimethyl-2-(dimethylamino)ethyl]indene,
[1,1-diphenyl-2-(dimethylamino)ethyl]indene,
[1-methyl-1-phenyl-2-(dimethylamino)ethyl]indene,
[1-tert-butyl-2-(dimethylamino)ethyl]indene,
9-(dimethylamino)methyl)fluorene, 9-(1-(2-dimethylamino) ethyl)fluorene,
9-(trimethylsilyl)-9-(dimethylamino)methyl)fluorene, and
9-(trimethylsilyl)-9-(1-(2-dimethylamino)ethyl)fluorene.

One method for preparing the cyclopentadienyl-type ligands, Method I, involves reacting fulvene compounds with a nucleophile, wherein the nucleophile is represented by the formula JA, wherein J is an alkali metal, preferably lithium, and wherein A is as described above.

The fulvene compound is represented by the general formula

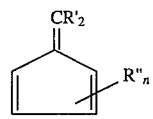

wherein each R' and R" is individually selected from the group consisting of alkyl, aryl, alkenyl, and alkoxy groups containing 1 to 20 carbon atoms, preferably 1 to 10 carbon atoms, halogen, and hydrogen; and wherein n is 1 to 4. Some examples of R' and R" include methyl, ethyl, propyl, isopropyl, butyl, tert-butyl, isobutyl, tert-butyl, amyl, isoamyl, hexyl, cyclohexyl, heptyl, octyl, nonyl, decyl, cetyl, 2-ethylhexyl, phenyl, and phenylmethyl.

Examples of typical fulvene compounds include 6-methylfulvene, 6-ethylfulvene, 6-isopropylfulvene, 6-butylfulvene, 6-tert-butylfulvene, 6-octylfulvene, 1,6-dimethylfulvene, 1,2,6-trimethylfulvene, 1,2,3,6-tetramethylfulvene,1,2,3,4,6-pentamethylfulvene.6,6-dimethylfulvene, 3,6,6-trimethylfulvene, 6,6-diethylfulvene, 6,6-diphenylfulvene, 6-ethyl-6-methylfulvene, 6-isopropyl-6-methylfulvene, 6,6-dibutylfulvene, 6,6-dioctylfulvene, 6-methyl-6-octylfulvene, 6-methyl-6-phenyl, 1,6,6-trimethylfulvene, 1,2,6,6-tetramethylfulvene, 1,2,3,6,6-pentamethylfulvene, and 1,2,3,4,6,6-hexamethylfulvene. Of the fulvene compounds, 6-methylfulvene, 6-phenylfulvene, 6-methyl-6-phenyl, 6-tert-butylfulvene, 6,6-dimethylfulvene, and 6,6-diphenylfulvene are preferred because they produce excellent results and are readily available.

The fulvene compounds can be prepared by any method known in the art. One such method is disclosed in J. Org. Chem., Vol. 49, No. 11, pp. 1849–53, 1984, the disclosure of which is incorporated herein by reference. Many such compounds are commercially available.

When reacting the fulvene compound and the nucleophile in Method I, generally the nucleophile compound will be present in an amount in the range of from about 0.1 mole to about 20 moles per mole of fulvene compound, preferably from 0.2 mole to about 10 moles per mole, and more preferably from 0.5 mole to 5 moles per mole of fulvene compound.

The reaction conditions for reacting the fulvene compound and the nucleophile in Method I are generally in the range of from about −100° C. to about 150° C., preferably from about −100° C. to about 125° C., and more preferably from −100° C. to about 100° C.

Generally a diluent is employed in Method I when reacting the fulvene compound and the nucleophile. Typical diluents include polar diluents such as for example tetrahydrofuran, or nonpolar diluents such as alkanes, cycloalkanes, aromatic hydrocarbons, and non-cyclic ethers. Some specific examples include toluene, heptane, hexane, and diethylether.

Another method for preparing the inventive cyclopentadienyl-type ligands, Method II, involves reacting a halocyclopentadienyl-type compound and the nucleophile JA, described above, wherein the halocyclopentadienyl-type compound is represented by the formula $ZCH_2X'$ wherein Z is a cyclopentadienyl-type group as described above and X' is a halide, preferably bromine or chlorine. The method has been found useful in preparing cyclopentadienyl-type ligands containing an unsubstituted or substituted fluorenyl group.

When reacting the halocyclopentadienyl-type compound and the nucleophile in Method II, generally the nucleophile compound will be present in an amount in the range of from about 0.1 mole to about 20 moles per mole of halocyclopentadienyl-type compound, preferably from 0.2 mole to about 10 moles per mole, and more preferably from 0.5 mole to 5 moles per mole of halocyclopentadienyl-type compound.

The reaction conditions for reacting the fulvene compound and the nucleophile in Method II are generally in the range of from about −100° C. to about 150° C., preferably from about −100° C. to about 125° C., and more preferably from −100° C. to about 100° C.

Generally a diluent is employed in Method II when reacting the halocyclopentadienyl-type compound and the nucleophile. Typical diluents include those described above, such as polar diluents such as for example tetrahydrofuran, or nonpolar diluents such as alkanes, cycloalkanes, aromatic hydrocarbons, and non-cyclic ethers. Some specific examples include toluene, heptane, hexane, and diethylether. Good results have been obtained with tetrahydrofuran and it is preferred.

Another method for preparing the inventive cyclopentadienyl-type ligands, Method III, involves (1) reacting a halosilane with an alkali metal salt of a cyclopentadienyl-type compound to form a silylcyclopentadienyl-type compound, (2) reacting the silylcyclopentadienyl-type compound with an alkali metal alkyl and methylene dichloride, to produce a chloromethylated silylcyclopentadienyl-type compound, and then (3) reacting the chloromethylated silylcyclopentadienyl-type compound with the above defined nucleophile, JA, to produce the cyclopentadienyl-type ligand. This method has been found especially useful in preparing cyclopentadienyl-type ligands containing a fluorenyl group. Silylfluorene compounds can be prepared by any method known such as disclosed in J. Am. Chem. Soc. 72 (1950) 1688, H. Gilman et al. the disclosure of which is herein incorporated by reference.

The halosilane compound employed in Method III is represented by the formula $X''Si(R^1)_3$, wherein $X''$ is a halide and wherein each $R^1$ is individually an alkyl group or hydrogen, wherein the alkyl group contains 1 to 20 carbon atoms, preferably 1 to 10, and more preferably 1 to 5 carbon atoms. Typical examples of $R^1$ include methyl, ethyl, propyl, isopropyl, butyl, tertbutyl, isobutyl, amyl, isoamyl, hexyl, cyclohexyl, heptyl, octyl, nonyl, decyl, cetyl, 2-ethylhexyl. Excellent results have been obtained with chlorotrimethylsilane and it is preferred.

Typically the alkali metal salts of cyclopentadienyl-type compounds employed in Method III can be prepared by dissolving a cyclopentadienyl-type compound in a suitable liquid diluent and then adding an alkali metal compound, such as an alkali metal alkyl. Techniques of forming such salts are known in the art. The alkali metal alkyls employed in preparing the alkali metal salt of the cyclopentadienyl-type compound can include any alkali metal alkyls capable of forming a suitable alkali metal salt. Typically the alkali metal alkyls would be selected from the alkyls of sodium, potassium, and lithium and the alkyl group would have 1 to 8, preferably 1 to 6 carbon atoms. The preferred alkali metal alkyls are lithium alkyls. Due to availability and efficacy, butyllithium is especially preferred. In preparing the alkali metal salt of the cyclopentadienyl-type compound, the amount of alkali metal alkyl employed is generally in the range of from about 0.5 mole to about 50 moles per mole of cyclopentadienyl-type compound, preferably 0.5 mole to 20 moles per mole of cyclopentadienyl-type compound.

When reacting the halosilane and the alkali metal salt of the cyclopentadienyl-type compound in step (1) of Method III, the halosilane is generally present in an amount in the range of from about 0.1 mole to about 20 moles per mole of cyclopentadienyl-type compound, preferably from 0.2 mole to about 10 moles per mole, and more preferably from 0.5 mole to 5 moles per mole of cyclopentadienyl-type compound.

When reacting the silylcyclopentadienyl-type compound, the alkali metal alkyl, and methylene dichloride in step of (2) Method III, the alkali metal alkyl and methylene dichloride are generally each present in an amount in the range of from about 0.1 mole to about 20 moles per mole of silylcyclopentadienyl-type compound, preferably from 0.2 mole to about 10 moles per mole, and more preferably from 0.5 mole to 5 moles per mole of silylcyclopentadienyl-type compound.

When reacting the chloromethylated silylcyclopentadienyl-type compound and the nucleophile in step (3) of Method III, the nucleophile is generally present in an amount in the range of from about 0.1 mole to about 20 moles per mole of chloromethylated silylcyclopentadienyl-type compound, preferably from 0.2 mole to about 10 moles per mole, and more preferably from 0.5 mole to 5 moles per mole of chloromethylated silylcyclopentadienyl-type compound.

Generally a diluent is employed when conducting the above described steps of Method III. Typical diluents include those described above such as for example polar diluents such as tetrahydrofuran, or nonpolar diluents such as alkanes, cycloalkanes, aromatic hydrocarbons, and non-cyclic ethers. Some specific examples include benzene, toluene, heptane, hexane, cyclohexane, and diethylether.

The reaction temperatures in steps (1), (2), and (3) of Method III are generally in the range of from about $-100°$ C. to about $150°$ C., preferably frown about $-100°$ C. to about $125°$ C., and more preferably from $-100°$ C. to about $100°$ C.

The inventive metallocenes are transition metal-containing trihalo complexes represented by the formula $ZAMX_3$ wherein Z is a cyclopentadienyl-type group as described above, A is as described above, M is a Group IVB or VB transition metal, preferably titanium, zirconium, hafnium or vanadium, more preferably zirconium or titanium, most preferably zirconium, and X is a halide, preferably X is chlorine.

The metallocenes are prepared by reacting an alkali metal alkyl as described above, the cyclopentadienyl-type ligand, and a metal halide compound represented by the formula $MX_4$, wherein M is a transition metal as described above, and X is a halide.

Examples of suitable metal halides include titanium tetrachloride, titanium tetraiodide, titanium tetrabromide, zirconium tetrachloride, zirconium tetraiodide, zirconium tetrabromide, hafnium tetrachloride, hafnium tetraiodide, hafnium tetrabromide, vanadium tetrachloride, vanadium tetraiodide, vanadium tetrabromide, and mixtures thereof. Excellent results have been obtained with titanium tetrachloride and zirconium tetrachloride and they are preferred.

The alkali metal alkyl is selected from the alkyls of sodium, potassium, and lithium and the alkyl group would have 1 to 8, preferably 1 to 6 carbon atoms. The preferred alkali metal alkyls are lithium alkyls. Due to availability and efficacy, butyllithium is especially preferred.

The relative amounts of the alkali metal alkyl, the cyclopentadienyl-type ligand, and the metal halide can vary broadly depending on the particular compounds employed. Generally the alkali metal alkyl is present in an amount in the range of from about 0.5 mole to about 2.0 moles per mole of cyclopentadienyl-type ligand, preferably in the range of from 0.5 mole to 1.75 moles, and more preferably from 0.5 mole to 1.5 moles per mole of cyclopentadienyl-type ligand. Generally the metal halide will be present in an amount in the range of from about 0.1 mole to about 50 moles per mole of cyclopentadienyl-type ligand, preferably in the range of from 0.2 mole to 20 moles, and more preferably from 0.5 mole to 10 moles per mole of cyclopentadienyl-type ligand.

Generally a diluent is employed when reacting the alkali metal alkyl, the cyclopentadienyl-type ligand, and the metal halide to form the metallocene. Typical diluents include polar diluents such as for example tetrahydrofuran, or nonpolar diluents such as alkanes, cycloalkanes, aromatic hydrocarbons, and non-cyclic ethers. Some specific examples include benzene, toluene, heptane, cyclohexane, hexane, and diethylether.

The temperature for reacting the alkali metal alkyl, the cyclopentadienyl-type ligand, and the metal halide is generally in the range of from about $-100°$ C. to about $100°$ C., preferably from about $-100°$ C. to about $80°$ C., and more preferably from $-100°$ C. to $60°$ C. Although the alkali metal alkyl, the cyclopentadienyl-type ligand, and the metal halide can be added in any order, it is preferred to first react the alkali metal alkyl with the cyclopentadienyl-type ligand to produce an alkali metal salt of the cyclopentadienyl-type ligand, and then react the alkali metal salt of the cyclopentadienyl-type ligand with the metal halide.

Typical examples of the inventive metallocenes include
[1-methyl-2-(dimethylphosphino)ethyl]cyclopentadienylzirconium trichloride,
[1-phenyl-2-(dimethylphosphino)ethyl]cyclopentadienylzirconium trichloride,
[1,1-dimethyl-2-(dimethylphosphino)ethyl]cyclopentadienylzirconium trichloride,
[1,1-diphenyl-2-(dimethylphosphino)ethyl]cyclopentadienylzirconium trichloride,
[1-methyl-1-phenyl-2-(dimethylphosphino)ethyl]cyclopentadienylzirconium trichloride,
[1-tert-butyl-2-(dimethylphosphino)ethyl]cyclopentadienylzirconium trichloride,
[1-methyl-2-(dimethylphosphino)ethyl]cyclopentadienylzirconium tribromide,
[1-phenyl-2-(dimethylphosphino)ethyl]cyclopentadienylzirconium tribromide,
[1,1-dimethyl-2-(dimethylphosphino)ethyl]cyclopentadienylzirconium tribromide,
[1,1-diphenyl-2-(dimethylphosphino)ethyl]cyclopentadienylzirconium tribromide,
[1-methyl-1-phenyl-2-(dimethylphosphino)ethyl]cyclopentadienylzirconium tribromide,
[1-tert-butyl-2-(dimethylphosphino)ethyl]cyclopentadienylzirconium tribromide,
[1-phenyl-2-(dimethylphosphino)ethyl]indenylzirconium trichloride,
[1,1-dimethyl-2-(dimethylphosphino)ethyl]indenylzirconium trichloride,
[1,1-diphenyl-2-(dimethylphosphino)ethyl]indenylzirconium trichloride,
[1-methyl-1-phenyl-2-(dimethylphosphino)ethyl]indenylzirconium trichloride,
[1-tert-butyl-2-(dimethylphosphino)ethyl]indenylzirconium trichloride,
9-(1-(2-dimethylphosphino)ethyl)fluorenylzirconium trichloride,
[(dimethylamino)methyl)]cyclopentadienylzirconium trichloride,
[(diethylamino)methyl)]cyclopentadienylzirconium trichloride,
[(dimethylamino)(phenyl)methyl)]cyclopentadienylzirconium trichloride,
[(diethylamino)(phenyl)methyl)]cyclopentadienylzirconium trichloride,
[(dimethylamino)(methyl)(phenyl)methyl)]cyclopentadienylzirconium trichloride,
[(diethylamino)(methyl)(phenyl)methyl) ]cyclopentadienylzirconium trichloride,
[1-phenyl-2-(dimethylamino)ethyl]cyclopentadienylzirconium trichloride,
[1-phenyl-2-(diethylamino)ethyl)cyclopentadienylzirconium trichloride,
[1-phenyl-2-(dimethylamino)ethyl]indenylzirconium trichloride,
[1,1-dimethyl-2-(dimethylamino)ethyl]indenylzirconium trichloride,
[1,1-diphenyl-2-(dimethylamino)ethyl]indenylzirconium trichloride,
[1-methyl-1-phenyl-2-(dimethylamino)ethyl]indenylzirconium trichloride,
[1-tert-butyl-2-(dimethylamino)ethyl]indenylzirconium trichloride,
9-(1-(2-dimethylamino)ethyl)fluorenylzirconium trichloride,
[1-methyl-2-(dimethylphosphino)ethyl]cyclopentadienyltitanium trichloride,
[1-phenyl-2-(dimethylphosphino)ethyl]cyclopentadienyltitanium trichloride,
[1,1-dimethyl-2-(dimethylphosphino)ethyl]cyclopentadienyltitanium trichloride,
[1,1-diphenyl-2-(dimethylphosphino)ethyl]cyclopentadienyltitanium trichloride,
[1-methyl-1-phenyl-2-(dimethylphosphino)ethyl]cyclopentadienyltitanium trichloride,
[1-tert-butyl-2-(dimethylphosphino)ethyl]cyclopentadienyltitanium trichloride,
[1-phenyl-2-(dimethylphosphino)ethyl]indenyltitanium trichloride,
[1,1-dimethyl-2-(dimethylphosphino)ethyl]indenyltitanium trichloride,
[1,1-diphenyl-2-(dimethylphosphino)ethyl]indenyltitanium trichloride,
[1-methyl-1-phenyl-2-(dimethylphosphino)ethyl]indenyltitanium trichloride,
[1-tert-butyl-2-(dimethylphosphino)ethyl]indenyltitanium trichloride,
9-(1-(2-dimethylphosphino)ethyl)fluorenyltitanium trichloride,
[(dimethylamino)methyl)]cyclopentadienyltitanium trichloride,
[(diethylamino)methyl)]cyclopentadienyltitanium trichloride,
[(dimethylamino)(phenyl)methyl)]cyclopentadienyltitanium trichloride,
[(diethylamino)(phenyl)methyl)]cyclopentadienyltitanium trichloride,
[(dimethylamino)(methyl)(phenyl)methyl)]cyclopentadienyltitanium trichloride, [(diethylamino)(methyl)(phenyl)methyl)]cyclopentadienyltitanium trichloride,
[1-phenyl-2-(diethylamino)ethyl]cyclopentadienyltitanium trichloride,
[1-phenyl-2-(dimethylamino)ethyl)cyclopentadienyltitanium trichloride,
[1-phenyl-2-(dimethylamino)ethyl]indenyltitanium trichloride,
[1,1-dimethyl-2-(dimethylamino)ethyl]indenyltitanium trichloride,
[1,1-diphenyl-2-(dimethylamino)ethyl]indenyltitanium trichloride,
[1-methyl-1-phenyl-2-(dimethylamino)ethyl]indenyltitanium trichloride,
[1-tert-butyl-2-(dimethylamino)ethyl]indenyltitanium trichloride,
9-(1-(2-dimethylamino)ethyl)fluorenyltitanium trichloride,
[1-methyl-2-(dimethylphosphino)ethyl]cyclopentadienylvanadium trichloride,
[1-phenyl-2-(dimethylphosphino)ethyl]cyclopentadienylvanadium trichloride,
[1,1-dimethyl-2-(dimethylphosphino)ethyl]cyclopentadienylvanadium trichloride,
[1,1-diphenyl-2-(dimethylphosphino)ethyl]cyclopentadienylvanadium trichloride,
[1-methyl-1-phenyl-2-(dimethylphosphino)ethyl]cyclopentadienylvanadium trichloride,
[1-tert-butyl-2-(dimethylphosphino)ethyl]cyclopentadienylvanadium trichloride,
[1-phenyl-2-(dimethylphosphino)ethyl]indenylvanadium trichloride,
[1,1-dimethyl-2-(dimethylphosphino)ethyl]indenylvanadium trichloride,
[1,1-diphenyl-2-(dimethylphosphino)ethyl]indenylvanadium trichloride,
[1-methyl-1-phenyl-2-(dimethylphosphino)ethyl]indenylvanadium trichloride,

[1-tert-butyl-2-(dimethylphosphino)ethyl]indenylvanadium trichloride,
9-(1-(2-dimethylphosphino)ethyl)fluorenylvanadium trichloride,
[(dimethylamino)methyl)]cyclopentadienylvanadium trichloride,
[(diethylamino)methyl)]cyclopentadienylvanadium trichloride,
[(dimethylamino)(phenyl)methyl)]cyclopentadienylvanadium trichloride,
[(diethylamino)(phenyl)methyl)]cyclopentadienylvanadium trichloride,
[(dimethylamino)(methyl)(phenyl)methyl)]cyclopentadienylvanadium trichloride,
[(diethylamino)(methyl)(phenyl)methyl)]cyclopentadienylvanadium trichloride,
[1-phenyl-2-(diethylamino)ethyl]cyclopentadienylvanadium trichloride,
[1-phenyl-2-(dimethylamino)ethyl)cyclopentadienylvanadium trichloride,
[1-phenyl-2-(dimethylamino)ethyl]indenylvanadium trichloride,
[1,1-dimethyl-2-(dimethylamino)ethyl]indenylvanadium trichloride,
[1,1-diphenyl-2-(dimethylamino)ethyl]indenylvanadium trichloride,
[1-methyl-1-phenyl-2-(dimethylamino)ethyl]indenylvanadium trichloride,
[1-tert-butyl-2-(dimethylamino)ethyl]indenylvanadium trichloride,
9-(1-(2-dimethylamino)ethyl)fluorenylvanadium trichloride,
[1-methyl-2-(dimethylphosphino)ethyl]cyclopentadienylhafnium trichloride,
[1-phenyl-2-(dimethylphosphino)ethyl]cyclopentadienylhafnium trichloride,
[1,1-dimethyl-2-(dimethylphosphino)ethyl]cyclopentadienylhafnium trichloride,
[1,1-diphenyl-2-(dimethylphosphino)ethyl]cyclopentadienylhafnium trichloride,
[1-methyl-1-phenyl-2-(dimethylphosphino)ethyl]cyclopentadienylhafnium trichloride,
[1-tert-butyl-2-(dimethylphosphino)ethyl]cyclopentadienylhafnium trichloride,
[1-phenyl-2-(dimethylphosphino)ethyl]indenylhafnium trichloride,
[1,1-dimethyl-2-(dimethylphosphino)ethyl]indenylhafnium trichloride,
[1,1-diphenyl-2-(dimethylphosphino)ethyl]indenylhafnium trichloride,
[1-methyl-1-phenyl-2-(dimethylphosphino)ethyl]indenylhafnium trichloride,
[1-tert-butyl-2-(dimethylphosphino)ethyl]indenylhafnium trichloride,
9-(1-(2-dimethylphosphino)ethyl)fluorenylhafnium trichloride,
[(dimethylamino)methyl)]cyclopentadienylhafnium trichloride,
[(diethylamino)methyl)]cyclopentadienylhafnium trichloride,
[(dimethylamino)(phenyl)methyl)]cyclopentadienylhafnium trichloride,
[(diethylamino)(phenyl)methyl)]cyclopentadienylhafnium trichloride,
[(dimethylamino)(methyl)(phenyl)methyl)]cyclopentadienylhafnium trichloride,
[(diethylamino)(methyl)(phenyl)methyl)]cyclopentadienylhafnium trichloride,
[1-phenyl-2-(diethylamino)ethyl]cyclopentadienylhafnium trichloride,
[1-phenyl-2-(dimethylamino)ethyl)cyclopentadienylhafnium trichloride,
[1-phenyl-2-(dimethylamino)ethyl]indenylhafnium trichloride,
[1,1-dimethyl-2-(dimethylamino)ethyl]indenylhafnium trichloride,
[1,1-diphenyl-2-(dimethylamino)ethyl]indenylhafnium trichloride,
[1-methyl-1-phenyl-2-(dimethylamino)ethyl]indenylhafnium trichloride,
[1-tert-butyl-2-(dimethylamino)ethyl]indenylhafnium trichloride, and
9-(1-(2-dimethylamino)ethyl)fluorenylhafnium trichloride.

The metallocenes can be used in combination with a suitable cocatalyst to produce catalyst systems for the polymerization of olefins. Examples of suitable cocatalysts include any of those organometallic cocatalysts which have in the past been employed in conjunction with transition metalcontaining olefin polymerization catalysts. Some typical examples include organometallic compounds of metals of Groups IA, IIA, and IIIB of the Periodic Table. Examples of such compounds include organometallic halide compounds, organometallic hydrides, and metal hydrides. Some specific examples include triethylaluminum, tri-isobutylaluminum, diethylaluminum chloride, diethylaluminum hydride, and the like. Other examples of known cocatalysts include the use of a stable non-coordinating counter anion such as disclosed in U.S. Pat. No. 5,155,080, e.g. using triphenyl carbenium tetrakis(pentafluorophenyl)boronate. Another example would be the use of a mixture of trimethylaluminum and dimethylfluoroaluminum such as disclosed by Zambelli et, *Macromolecules*, 22, 2186 (1989).

Currently, organoaluminoxane cocatalysts are the preferred cocatalysts. Various techniques are known for making organoaluminoxanes. One technique involves the controlled addition of water to a trialkylaluminum. Another technique involves combining a trialkylaluminum and a hydrocarbon with a compound containing water of adsorption or a salt containing water of crystallization. Many suitable organoaluminoxanes are commercially available.

Typically the organoaluminoxanes comprise oligomeric, linear and/or cyclic hydrocarbyl aluminoxanes having repeating units of the formula

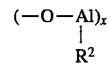

wherein each $R^2$ is a hydrocarbyl group, preferably an alkyl group containing 1–8 carbon atoms, x is 2 to 50, preferably 4 to 40, and more preferably 10 to 40. Typically $R^2$ is predominantly methyl or ethyl. Preferably at least about 30 mole percent of the repeating groups have an $R^2$ which is methyl, more preferably at least 50 mole percent, and still more preferably at least 70 mole percent. Generally in the preparation of an organoaluminoxane, a mixture of linear and cyclic compounds is obtained. Organoaluminoxanes are commercially available in the form of hydrocarbon solutions, generally aromatic hydrocarbon solutions.

A solid organoaluminoxy product can be prepared by reacting an organoaluminoxane and an oxygen-containing compound selected from the group consisting of organo boroxines, organic boranes, organic peroxides, alkylene oxides, and organic carbonates.

The amount of organoaluminoxane relative to the metallocene can vary broadly depending upon the particular catalyst selected and the results desired. Typically, the organoaluminoxane is present in the amount of about 0.5 moles to about 10,000 moles aluminum per mole of metal in the metallocene, preferably about 10 moles to about 5,000 moles, and more preferably 50 moles to 5,000 moles.

The above described steps for preparing the catalyst system are generally conducted in the presence of a solvent or a diluent. Typical solvents or diluents include for example tetrahydrofuran, heptane, hexane, cyclohexane, benzene, toluene, and diethylether.

A variety of olefin compounds are suitable for use as monomers in the polymerization process of the present invention. Olefins which can be employed include linear, branched, and cyclic aliphatic olefins. While the invention would appear to be suitable for use with any aliphatic olefin known to be employed with metallocenes, those olefins having 2 to 18 carbon atoms are most often used. Ethylene and propylene are especially preferred. Often a second olefin (comonomer) having from 2 to 12 carbon atoms, preferably from 4 to 10 carbon atoms can be employed. Typical comonomers include propylene, 1-butene, 1-pentene, 4-methyl-1-pentene, 2-pentene, 1-hexene, 2-hexene, cyclohexene, 1-heptene, and dienes such as butadiene.

The polymerization processes according to the present invention can be performed either batchwise or continuously. The olefin, metallocene, and organoaluminoxane cocatalyst can be contacted in any order. It is preferred that the metallocene and the organoaluminoxane are contacted prior to contacting with the olefin. Generally a diluent such as isobutane is added to the reactor. The reactor is heated to the desired reaction temperature and olefin, such as ethylene, is then admitted and maintained at a partial pressure within a range of from about 0.5 MPa to about 5.0 MPa (70–725 psi) for best results. At the end of the designated reaction period, the polymerization reaction is terminated and the unreacted olefin and diluent vented. The reactor can be opened and the polymer can be collected as a free-flowing white solid and dried to obtain the product.

The reaction conditions for contacting the olefin and the catalyst system can vary broadly depending on the olefin employed, and are those sufficient to polymerize the olefins. Generally the temperature is in the range of about 20° C. to about 300° C., preferably in the range of 50° C. to 150° C. The pressure is generally in the range of from about 0.5 MPa to about 5.0 MPa (70–725 psi).

The present invention can be employed in any olefin polymerization process known such as gas phase particle form, slurry type, or solution phase polymerizations. A preferred type particle form polymerization involves a continuous loop reactor which is continuously charged with suitable quantities of diluent, catalyst system, and polymerizable compounds in any desirable order. Typically the polymerization will include a higher alpha-olefin comonomer and optionally hydrogen. Generally the particle form polymerization is conducted at a temperature in the range of about 50° C. to about 110° C., although higher and lower temperatures can be used. Polyethylenes of varying molecular weight distribution can be produced by varying the amount of hydrogen. The reaction mixture containing polymer can be continuously withdrawn and the polymer recovered as appropriate, generally by flashing the diluent and unreacted monomers and drying the resulting polymer.

The following examples serve to show the present invention in detail by way of illustration and not by way of limitation.

EXAMPLES

The examples demonstrate the effectiveness of the inventive processes in preparing new cyclopentadienyl-type ligands and metallocene compounds and the use of such metallocene compounds in catalyst systems.

Example 1

Cyclopentadienyl-type Ligands

Cyclopentadienyl-type ligands were prepared employing Method I by reacting 19 mmol $LiCH_2P(CH_3)_2$ dissolved in 70 mL tetrahydrofuran (THF) with 19 mmol fulvene compound dissolved in 25 mL THF at 0° C. The fulvene solution was added dropwise over a period of 30 to 90 minutes. The reaction mixture was stirred for 90 minutes at 0° C. The solvent was removed under vacuum and the residue was hydrolyzed with aqueous $NH_4Cl$ solution and extracted with 2×30 mL pentane. The extract was filtered over anhydrous $An_2SO_4$ and dried under vacuum. The fulvene compounds employed, the resulting cyclopentadienyl-type ligands, and the respective yields are indicated below:

6-phenylfulvene was employed in preparing [1-phenyl-2-(dimethylphosphino)ethyl]cyclopentadiene and produced 72.9% yield of orange oil;

6,6-dimethylfulvene was employed in preparing [1,1-dimethyl-2-(dimethylphosphino)ethyl]cyclopentadiene and produced a yield of 36.0% as a yellow oil;

6,6-diphenylfulvene was employed in preparing [1,1-diphenyl-2-(dimethylphosphino)ethyl]cyclopentadiene which yielded 35.0 as an orange oil; and 6-tert-butylfulvene was employed in preparing [1-tert-butyl-2-(dimethylphosphino)ethyl]cyclopentadiene and produced a 63.2% yield as an orange oil.

Example 2

Metallocenes

Metallocene compounds were prepared by reacting the cyclopentadienyl-type ligands with metal halides. In a typical example, 1.60 g (5.28 mmol) [1,1-diphenyl-2-(dimethylphosphino)ethyl]cyclopentadiene, prepared as described in Example 1, dissolved in 60 mL hexane was reacted with 3.30 mL (5.28 mmol) n-BuLi (1.6M in hexane). The n-BuLi was added dropwise over a period of 30 minutes at room temperature. The reaction mixture containing orange precipitate was stirred until the evolution of butane gas ceased. The reaction mixture was cooled to −20° C. employing an isopropyl alcohol-dry ice bath and then 0.87 mL (7.92 mmol) anhydrous $TiCl_4$ was added dropwise over 20 minutes. The mixture was stirred for 2 hours at −20° C. The resulting brown suspension was filtered and washed with 20 mL of hexane. The filtrate was concentrated under vacuum and placed in a refrigerator. A yellow-green precipitate separated from the mother liquor (solid I). The brown solid obtained by filtration was washed with large amounts of toluene and $CH_2Cl_2$. The resulting solution was dried to give a yellow solid (solid II). Solids I and II were combined to give 0.81 g (1.76 mmol) [1,1-diphenyl-2-(dimethylphosphino)ethyl]cyclopentadienyltitanium trichloride for an overall yield of 33.3%. The metallocene compounds [1-tert-butyl-2-(dimethylphosphino)ethyl]cyclopentadienyltitanium trichloride, [1-phenyl-2-(dimethylphosphino)ethyl]cyclopentadienyltitaniumtrichloride, and [1,1-dimethyl-2-(dimethylphosphino)ethyl]cyclopentadienyltitanium trichloride were prepared in a similar fashion employing the respective cyclopentadienyl-type ligands.

Example 3

A cyclopentadienyl-type ligand containing fluorene was prepared as follows employing Method II. To a solution of 1.2 g LiCH$_2$P(CH$_3$)$_2$ in 50 mL THF was added 3.0 g (bromomethyl)fluorene in 50 mL THF at −78° C. over a period of one hour. The mixture was stirred an additional 30 minutes at room temperature. Filtration of the mixture gave a clear yellow solution.

A fluorene-containing metallocene was prepared by reacting the thus prepared yellow solution with 7.1 mL n-butyllithium (1.5M in hexane). After stirring for 2 hours at room temperature the solvent was removed and then 30 mL ether was added. Then a solution of 2.5 g ZrCl$_4$ in 10 mL ether was added at −78° C. The mixture was stirred for 10 minutes at −78° C. and one hour at room temperature. Then the ether was removed and 60 mL hexane was added. The hexane solution was filtered over An$_2$SO$_4$. The solvent was removed and the residue was extracted with 25 mL toluene and the metallocene was crystallized at −78° C.

Example 4

A cyclopentadienyl-type ligand containing fluorene was prepared as follows employing Method III. In a reaction vessel 8.3 g (0.05 mol) fluorene in 150 mL ether was reacted with 31.3 ml (0.05 mol) butyllithium (1.5M in hexane) and then with 6.3 mL (0.05 mol) SiMe$_3$Cl in 50 mL pentane to form trimethylsilylfluorene. Then 6.8 g (0.03 mol) of the thus produced trimethylsilylfluorene was reacted with 18.7 mL (0.03 mol) butyllithium (1.6M in hexane) and 8.12 mL (0.13 mol) CH$_2$Cl$_2$ in 100 mL pentane for two hours at room temperature to form (Me$_3$Si)(ClCH$_2$)Flu, where Me is methyl and Flu is fluorene. The solvent was removed leaving a yellow residue. Then 2.5 g (0.009 mol) (Me$_3$Si)(ClCH$_2$)Flu in 30 mL THF was reacted with 0.71 g (0.009 mol) LiCH$_2$PMe$_2$ in 50 mL THF with stirring at −78° C. to form (Me$_3$Si)(Me$_2$P(CH$_2$)$_2$)Flu. The (Me$_3$Si)(ClCH$_2$)Flu was added over a period of two hours and the reaction was allowed to continue an additional three hours at −78° C. and then overnight at room temperature. The solvent was removed and the hexane gave 1.35 g of dark yellow oily product.

The fluorene-containing metallocene was prepared by reacting 1.35 g (0.004 mol) (Me$_3$Si)(Me$_2$P(CH$_2$)$_2$)Flu in 50 mL hexane with 3.5 mL (0.006 mol) butyllithium (1.5M in hexane) and 1.1 g (0.004 mol) ZrCl$_4$ in 10 mL hexane. The ZrCl$_4$ was added over a period of 2 hours at −78° C. and then stirred for an additional hour at 25° C. The reaction mixture was filtered over An$_2$SO$_4$. The solvent was removed and a yellow-brown fine powder was obtained

Example 5

Polymerizations

Several catalyst systems were employed in the polymerization of ethylene. The conditions included a total pressure of 450 psig, a partial pressure of H$_2$ of 10 psig, and a temperature of 90° C. The polymerization was conducted in 2 liters isobutane diluent for one hour.

The catalyst systems employed in Runs 101–104 were prepared by contacting 10 mL MAO from Shering with 0.003–0.005 g of each metallocene. The metallocene [1,1-dimethyl-2-(dimethylphosphino)ethyl]cyclopentadienyltitanium trichloride was employed in Runs 101 and 102. The metallocene [1,1-diphenyl-2-(dimethylphosphino)ethyl]cyclopentadienyltitanium trichloride was employed in Runs 103 and 104. The polymerizations in Runs 101–104 were conducted employing 3.0 mL of each catalyst system.

The catalyst system in Run 105 was prepared by contacting 9.38 mL MAO from Ethyl, 0.62 mL toluene and 0.0123 g of the metallocene [1,1-dimethyl-2-(dimethylphosphino)ethyl]cyclopentadienylzirconium trichloride.

The results are tabulated in the Table below. Al/M is the moles aluminum/mole transition metal employed. Methylaluminoxane was employed as the cocatalyst. Hexene is the grams hexene-1 employed as comonomer. Productivity is the g polyethylene/g transition metal·hour. MI is the melt index in g/10 min. run according to ASTM 1238. Density is g/cc measured according to ASTM 1505.

TABLE

| Run | Metallocene | Al/M | Hexene grams | Productivity g PE/g M·hr | MI g/10 min. | Density g/cc |
|---|---|---|---|---|---|---|
| 101 | A* | 730 | 0 | 19,000 | 0.001 | 0.9714 |
| 102 | A* | 730 | 50 | 13,000 | 0 | 0.9791 |
| 103 | B* | 1000 | 0 | 8,000 | 0 | 0.9653 |
| 104 | B* | 1000 | 50 | 6,500 | 0 | 0.9763 |
| 105 | C* | 470 | 0 | 364,000 | 1.91 | 0.9688 |

*A is [1,1-dimethyl-2-(dimethylphosphino)ethyl]cyclopentadienyltitanium trichloride
*B is [1,1-diphenyl-2-(dimethylphosphino)ethyl]cyclopentadienyltitanium trichloride
*C is [1,1-dimethyl-2-(dimethylphosphino)ethyl]cyclopentadienylzirconium trichloride That which is claimed is:

1. A process for preparing a cyclopentadienyl-type ligand comprising:

(1) reacting a halosilane with an alkali metal salt of a cyclopentadienyl-type compound to form a silylcyclopentadienyl-type compound, wherein said halosilane compound containing a cyclopentadienyl-type group is represented by the formula X"Si(R$^1$)$_3$, wherein X" is a halide and wherein each R$^1$ is individually an alkyl group containing 1 to 20 carbon atoms or hydrogen, wherein said cyclopentadienyl-type group is an unsubstituted cyclopentadienyl, substituted cyclopentadienyl, unsubstituted indenyl, substituted indenyl, unsubstituted fluorenyl, or substituted fluorenyl group, wherein the substituents on said cyclopentadienyl-type group are hydrocarbyl groups containing 1 to 12 carbon atoms, alkoxy groups containing 1 to 12 carbon atoms, trialkylsilyl groups where each alkyl group contains 1 to 12 carbon atoms, alkyl halide groups where the alkyl group contains 1 to 12 carbon atoms, or halide;

(2) reacting said silylcyclopentadienyl-type compound with an alkali metal alkyl containing 1 to 8 carbon atoms and methylene chloride, to produce a chloromethylated silylcyclopentadienyl-type compound; and then (3) reacting said chloromethylated silylcyclopentadienyl-type compound with a nucleophile to produce said cyclopentadienyl-type ligand, wherein said nucleophile is represented by the formula JA, wherein J is an alkali metal, wherein A is —YPR$_2$, —YNR$_2$, or —NR$_2$, wherein Y is an alkylene group containing 1 to 24 carbon atoms, wherein each R is individually selected from alkyl groups containing 1 to 20 carbon atoms.

2. A process according to claim 1 wherein said halosilane is chlorotrimethylsilane and wherein J is lithium.

3. A process according to claim 1 wherein said cyclopentadienyl-type group is an unsubstituted fluorenyl or substituted fluorenyl group.

4. A process according to claim 3 wherein Y contains 1 to 20 carbon atoms and wherein each R contains 1 to 10 carbon atoms.

5. A process according to claim 4 wherein Y contains 1 to 16 carbon atoms and wherein each R contains 1 to 5 carbon atoms.

6. A process according to claim 5 wherein Y is an unsubstituted or substituted methylene or ethylene group and wherein each R is methyl.

7. A process according to claim 6 wherein the substituents on said cyclopentadienyl-type group are alkyl groups containing 1 to 10 carbon atoms.

8. A process according to claim 7 wherein the substituents are alkyl groups containing 1 to 6 carbon atoms.

9. A process according to claim 8 wherein A is $-CH_2P(CH_3)_2$.

* * * * *